United States Patent
Nevoral et al.

(10) Patent No.: US 10,485,584 B2
(45) Date of Patent: Nov. 26, 2019

(54) SUPPLEMENT FOR CULTIVATION OF MAMMALIAN EMBRYOS

(71) Applicants: Lekarska fakulta v Plzni, Univerzita Karlova (Faculty of Medicine in Pilsen, Charles University), Pilsen (CZ); The Curators of the University of Missouri, Columbia, MO (US); Chonbuk National University, Division of Biotechnology, College of Environmental and Bioresources, Jeollabuk-do (KR); Ceska zemedelska univerzita v Praze, Prague 10-Suchdol (CZ); Institute of Animal Science, Prague 6-Uhrineves (CZ)

(72) Inventors: Jan Nevoral, Plzen (CZ); Young-Joo Yi, Iksan-si (KR); Katerina Zamostna-Adamkova, Prague-Stodulky (CZ); Jaroslav Petr, Prague-Uhrineves (CZ); Peter Sutovsky, Columbia, MO (US); Milena Kralickova, Pilsen (CZ)

(73) Assignees: Lekarska fakulta v Plzni, Univerzita Karlova (Faculty of Medicine in Pilsen, Charles University), Pilsen (CZ); The Curators of the University of Missouri, Columbia, MO (US); Chonbuk National University, Division of Biotechnology, College of Environmental and Bioresources, Jeollabuk-Do (KR); Ceska zemedelska univerzita v Praze, Prague 6-Suchdol (CZ); Institute of Animal Science, Prague 10-Uhrineves (CZ)

( * ) Notice: Subject to any disclaimer, the term of this patent is extended or adjusted under 35 U.S.C. 154(b) by 264 days.

(21) Appl. No.: 15/617,719

(22) Filed: Jun. 8, 2017

(65) Prior Publication Data
US 2018/0353209 A1    Dec. 13, 2018

(51) Int. Cl.
*A61B 17/435* (2006.01)
*C12N 5/073* (2010.01)

(52) U.S. Cl.
CPC .......... *A61B 17/435* (2013.01); *C12N 5/0604* (2013.01); *C12N 2501/999* (2013.01)

(58) Field of Classification Search
CPC ............ A61B 17/435; C12N 2501/999; C12N 5/0604
See application file for complete search history.

(56) References Cited

U.S. PATENT DOCUMENTS

2018/0179491 A1*  6/2018  Kim ................... C12N 5/0606

OTHER PUBLICATIONS http://www.enzolifesciences.com/BML-GR359/bml-278/Accessed Mar. 22, 2019 (Year: 2009).*

* cited by examiner

Primary Examiner — Christine H Matthews
Assistant Examiner — Joshua Daryl D Lannu
(74) Attorney, Agent, or Firm — Notaro, Michalos & Zaccaria P.C.

(57) ABSTRACT

Media, kits, and methods for cultivation of mammalian embryos from fertilized oocyte stage to blastocyst stage in the presence of N-benzyl-3,5-dicarbethoxy-4-phenyl-1,4-dihydropyridine. The use of this supplement improves the early embryonic development, in particular the quality of zygotes and the blastocyst formation. The supplemented media can be used with pigs, humans, or other mammals N-benzyl-3,5-dicarbethoxy-4-phenyl-1,4-dihydropyridine may be added to known media, and used for with vitro fertilization methods.

18 Claims, 1 Drawing Sheet

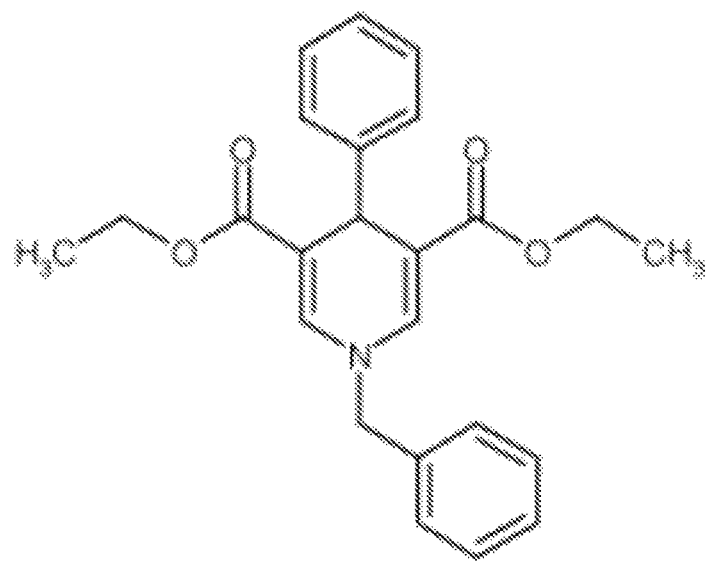

SUPPLEMENT FOR CULTIVATION OF MAMMALIAN EMBRYOS

This invention was made with government support under Grant No. 2015-67015-23231, awarded by the U.S. Department of Agriculture's (USDA) National Institute for Food and Agriculture. The government has certain rights in the invention.

FIELD OF THE INVENTION

The present invention relates to an improved process of in vitro cultivation of mammalian embryos, and to the use of a novel supplement in the cultivation process.

BACKGROUND

Currently, in vitro fertilization and in vitro cultivation of embryos until the blastocyst stage are common techniques used in the framework of assisted reproductive technology in animals and assisted reproductive therapy (ART) in humans. The blastocyst stage is considered to be optimal for the transfer of the embryo into the uterus.

The conditions of in vitro cultivation are decisive factors for successfully achieving the blastocyst stage. Accordingly, long-term development of in vitro conditions includes the composition of regulated atmosphere (5% $CO_2$, eventually regulated $O_2$ due to $N_2$ supplementation) and especially the balance of used compounds in media, designed for in vitro oocyte maturation and fertilization as well as for in vitro embryo culture.

The improvement of the culture media for in vitro embryo culture is crucial because embryos are placed there for several days while embryonic development is dramatically progressed. Therefore, embryo culture media are sometimes supplemented with antioxidants and/or substances specifically affecting key factors of the early embryonic development. Suitable supplements may significantly improve the success rate of in vitro production of transferable embryos and hence the efficiency of assisted reproduction procedures, thus, there is a continuing need for identification of novel suitable supplements improving the success rate and the quality of transferable embryos.

SUMMARY OF THE INVENTION

The present invention relates to a process for in vitro cultivation of mammalian embryos which comprises the step of cultivating mammalian embryos from fertilized oocytes (presumed zygotes), preferably up to the blastocyst stage, in the presence of N-benzyl-3,5-dicarbethoxy-4-phenyl-1,4-dihydropyridine ($C_{24}H_{25}NO_4$). The step of cultivating mammalian embryos from fertilized oocytes (presumed zygotes), preferably up to the blastocyst stage, in the presence of N-benzyl-3,5-dicarbethoxy-4-phenyl-1,4-dihydropyridine comprises more particularly: providing fertilized oocytes, contacting them with a culture medium for in vitro cultivating mammalian embryos from the zygote stage, preferably up to the blastocyst stage, said medium containing N-benzyl-3,5-dicarbethoxy-4-phenyl-1,4-dihydropyridine, and maintaining the fertilized oocytes in the medium. The fertilized oocytes may be maintained in the medium until they reach the blastocyst stage, or until they reach an earlier stage deemed suitable for embryo transfer, freezing, or other uses. The medium can be changed during the time of the cultivation for a fresh one, preferably still containing N-benzyl-3,5-dicarbethoxy-4-phenyl-1,4-dihydropyridine.

The inventors of this invention have found that N-benzyl-3,5-dicarbethoxy-4-phenyl-1,4-dihydropyridine surprisingly improves the early embryonic development, in particular the quality of zygotes and the blastocyst formation.

The step of cultivating mammalian embryos from the fertilized oocyte stage, preferably up to the blastocyst stage, in the presence of N-benzyl-3,5-dicarbethoxy-4-phenyl-1,4-dihydropyridine comprises contacting the fertilized oocyte with a culture medium comprising N-benzyl-3,5-dicarbethoxy-4-phenyl-1,4-dihydropyridine and maintaining the fertilized oocyte in said medium comprising N-benzyl-3,5-dicarbethoxy-4-phenyl-1,4-dihydropyridine, preferably until it develops into blastocyst stage.

Furthermore, the present invention encompasses use of N-benzyl-3,5-dicarbethoxy-4-phenyl-1,4-dihydropyridine for in vitro cultivation of mammalian embryos. N-benzyl-3,5-dicarbethoxy-4-phenyl-1,4-dihydropyridine can be used in procedures corresponding to standard protocols of in vitro fertilization and embryo culture.

Moreover, the present invention includes a culture medium for in vitro culture of mammalian embryos, which comprises N-benzyl-3,5-dicarbethoxy-4-phenyl-1,4-dihydropyridine as a key supplement.

The invention includes culture media comprising N-benzyl-3,5-dicarbethoxy-4-phenyl-1,4-dihydropyridine. For example, culture media comprising a buffer solution (e.g. a basic salt solution), one or more salts, one or more amino acids, and N-benzyl-3,5-dicarbethoxy-4-phenyl-1,4-dihydropyridine. Porcine zygote medium 3 (PZM3 medium) supplemented with N-benzyl-3,5-dicarbethoxy-4-phenyl-1,4-dihydropyridine is a useful embodiment. Methods and kits for mammalian embryo growth and in vitro fertilization (IVF) procedures (in humans or other mammalian animals) using or including such culture media are also contemplated. "Standard protocol of in vitro fertilization and embryo culture" should be understood as including known protocols for animal embryo production, for example using media based on the following: NCSU-23 (Petters and Wells 1993), PZM3 (Yoshioka et al. 2002), TCM199 (Shemesh et al. 1979), CZB (Chatot et al., 1989), BM (Kwon et al. 2013), SOM and KSOM (Summers, 2013). In addition to references discussing animal embryos, the aforementioned "standard protocols" also include manuals for human embryo production (e.g. Gardner and Lane, 2007).

Yet further, the present invention includes a culture medium for in vitro culture of mammalian embryos from the zygote stage to the blastocyst stage, which comprises N-benzyl-3,5-dicarbethoxy-4-phenyl-1,4-dihydropyridine as a supplement.

The present invention also includes a kit comprising a culture medium for in vitro culture of mammalian embryos from the zygote stage to the blastocyst stage, and at least N-benzyl-3,5-dicarbethoxy-4-phenyl-1,4-dihydropyridine as a supplement. The kit may also comprise further supplements.

In some embodiments, N-benzyl-3,5-dicarbethoxy-4-phenyl-1,4-dihydropyridine is used in the concentration of 0.3 to 30 µM, 0.3 to 10 µM, more preferably up to 5 µM, most preferably of 0.3 to 3 µM.

N-benzyl-3,5-dicarbethoxy-4-phenyl-1,4-dihydropyridine of sufficient purity is commercially available.

A "culture medium for in vitro culture of mammalian embryos from the zygote stage to the blastocyst stage" means a culture medium which is suitable for in vitro culture of mammalian embryos from the zygote stage up to and including blastocyst stage. Any culture media, known as being suitable for cultivation of early-stage mammalian embryos, may be used in the present invention. Examples of such culture media include M199, TCM-199, NCSU, KSOM, CZB. In one embodiment, the culture medium is PZM3 medium (Yoshioka et al. 2002).

Other known supplements can be used in combination with the novel supplement, N-benzyl-3,5-dicarbethoxy-4-phenyl-1,4-dihydropyridine. Accordingly, polyphenolic compounds (i.e. resveratrol, curcumin, quercetin and others), their precursors (such as polydatin), melatonin and/or donors of gasotransmitters (nitric oxide, hydrogen sulfide) are potent substances combinable with invention compound and resulting to improvement of embryo development, lifespan and quality.

The present invention is applicable to any mammalian embryos, but can be considered to be particularly useful for pigs, mice, rats, and both domestic (dogs, cats) and farm animals (cattle, sheep, goats and horses) as well as humans. Use with human zygotes, cells, and embryos for both research and assisted reproduction is contemplated. Use with mammals for veterinary, reproductive, and agricultural purposes is also contemplated.

BRIEF DESCRIPTION OF THE FIGURES

FIG. 1 is a chemical structural formula of N-benzyl-3,5-dicarbethoxy-4-phenyl-1,4-dihydropyridine.

DETAILED DESCRIPTION AND EXAMPLES

Collection and In Vitro Maturation (IVM) of Porcine Oocytes

Porcine ovaries were obtained from 6- to 8-month-old non-cycling gilts (a crossbreed of Landrace x Large White) at the local slaughterhouse (Jatky Plzen a.s., Plzen, Czech Republic) and transported to laboratory at 39° C. Cumulus-oocyte complexes (COCs) were collected from ovarian follicles with a diameter of 2-5 mm by aspiration with a 20-gauge needle and handled in HEPES-buffered Tyrode lactate medium containing 0.01% (w/v) polyvinyl alcohol (TL-HEPES-PVA). Only fully grown oocytes with evenly dense cytoplasm, surrounded by compact cumuli, were selected for IVM and washed in maturation medium. The medium used for IVM was modified tissue culture medium (mTCM) 199 (Gibco, Life Technologies, UK) supplemented with 0.1% PVA, 3.05 mM D-glucose, 0.91 mM sodium pyruvate, 0.57 L-cysteine, 0.5 µg·mL$^{-1}$ LH (Sigma-Aldrich, USA), 0.5 µg·mL$^{-1}$ FSH (Sigma), 10 ng·mL$^{-1}$ epidermal growth factor (EGF; Sigma), 10% porcine follicular fluid, 75 µg·mL$^{-1}$ penicillin G and 50 µg·mL$^{-1}$ streptomycin. After 22 h of culture, the COCs were cultured in TCM199 without LH and FSH for an additional 22 h. The COCs were cultured in 500 µL of the medium covered by mineral oil in a four-well Petri dish (Nunc, Denmark), at 39° C. and 5% $CO_2$ in air (Abeydeera et al. Theriogenology 50:747-756, 1998).

In Vitro Fertilization (IVF) and Culture (IVC) of Porcine Oocytes and Zygotes

After 44 h of IVM, cumulus cells were removed with 0.1% hyaluronidase in TL-HEPES-PVA and the metaphase II (MII) oocytes with extruded first polar body were selected for IVF. The oocytes were washed three-times with modified Tris-buffered medium (mTBM; Abeydeera et al. Theriogenology 50:747-756, 1998) with 0.2% bovine serum albumin (BSA; A7888; Sigma) and placed into 100 µL drops of mTBM, covered with mineral oil in a 35 mm Petri dish. The dishes were allowed to equilibrate at 38.5° C. and 5% $CO_2$ for 30 min before spermatozoa were added for fertilization. Spermatozoa were prepared as follows: 1 mL liquid semen preserved in BTS-based extender was washed twice in phosphate buffered saline (PBS) with 0.1% PVA (PBS-PVA) at 1500 rpm for 5 min. The last wash was supplemented with MitoTracker CMTRos (400 nM; M7510, Invitrogen) for 10 min at 39° C., used to tag sperm mitochondria that associate with the paternal pronucleus inside the fertilized oocytes. Labeled spermatozoa were resuspended in mTBM (2.5-5×10$^{-7}$ spermatozoa mL$^{-1}$) and 1 µL of this sperm suspension was added to the medium containing the oocytes to give a final sperm concentration of 2.5 or 5×10$^5$ spermatozoa mL$^{-1}$. Oocytes were co-incubated with spermatozoa for 5 to 6 h at 38.5° C. and 5% $CO_2$ in air. Thereafter, oocytes were washed and transferred into 100 µL PZM3 medium (Yoshioka et al. Biol Reprod 66:112-119, 2002) containing 0.4% BSA (A6003; Sigma) for further culture for 22 h. Simultaneously, presumed zygotes were cultured in 500 µL of PZM3 medium for 144 hrs to reach blastocyst stage. PZM3 was supplemented with the object of invention, i.e. N-benzyl-3,5-dicarbethoxy-4-phenyl-1,4-dihydropyridine, diluted in DMSO. Vehicle control contained DMSO only in equal concentration (0.1%). Tested concentrations of the compound are 1.5 and 3 µM, based on preliminary experiments evaluating the range 0.3-30 µM (see Table 1).

Evaluation of Fertilization Rate, Monospermy and Embryonic Development

Within the imaging of 22 h zygotes, an assessment of penetration rate, creation of paternal pronucleus/pronuclei and monospermic fertilization was performed. Embryo cleavage was assessed by microscopy at 144 h of IVC. After 144 h of IVC, embryos were fixed in 2% formaldehyde for 40 min at room temperature (RT), washed three times with PBS, permeabilized with PBS-Triton X-100 for 30 min, and stained with 2.5 µg/mL DAPI (DNA staining; Molecular Probes, Eugene, Oreg., USA) for 40 min. Embryo cleavage, blastocyst formation, and cell number per blastocyst were assessed under an Eclipse Ci fluorescence microscope (Nikon Co., Tokyo, Japan).

Statistics

Data are presented as the mean±S.E.M. of at least three independent experiments. The general linear models (GLM) procedure in SAS package 9.3 (SAS Institute Inc., Cary, N.C., USA) was used to analyze data from all experiments. Significant differences among groups were determined using Sheffe's test. Duncan's multiple range test was performed to compare values of blastocyst formation at 144 h of IVC. P<0.05 was considered to be statistically significant.

The results are presented in Tables 1 to 3. The tables summarize the preliminary results of testing of the supplement of the invention in a broad concentration range (Table 1) as well as complete results of a narrower range of concentrations of the supplement (Table 2 and 3). In addition to this, the effect of the supplement of the invention has been compared with resveratrol (Table 3), a known compound with known embryo-protective effect.

TABLE 1

Preliminary data of IVF and zygote quality in the presence of N-benzyl-3,5-dicarbethoxy-4-phenyl-1,4-dihydropyridine. Zygote quality is expressed by methylation and acetylation of histone H3 on lysine K9 (H3K9me2/3 and H3K9ac, respectively) in pronuclear chromatin (related to untreated vehicle, DMSO = 1). Methylation of H3K9 accompanies chromatin stability while acetylation is associated with euchromatin establishment and makes DNA break-prone.

|  |  | H3K9me2/3 | H3K9ac |
|---|---|---|---|
| DMSO (%, [v/v]) | 0.5 | 1.0 | 1.0 |
| Supplement of the invention ($\mu$M) | 0.3 | 2.72 | 0.61 |
|  | 3.0 | 1.64 | 0.63 |
|  | 30 | 0.76 | 1.36 |

TABLE 2

Results of IVF after 22 hr IVC in the presence of N-benzyl-3,5-dicarbethoxy-4-phenyl-1,4-dihydropyridine

|  |  | No. of fertilized oocytes | No. of penetrated oocytes (mean % ± SEM) | No. of oocyte with PPN (mean % ± SEM) | No. of monospermic fertilization (mean % ± SEM) |
|---|---|---|---|---|---|
| DMSO (%, [v/v]) | 0.5 | 195 | 79 (40.5 ± 9.4) | 50 (63.3 ± 12.6) | 42 (53.2 ± 12.5) |
| Supplement of the invention ($\mu$M) | 3.0 | 215 | 92 (42.8 ± 9.5) | 76 (82.6 ± 6.7)* | 39 (42.4 ± 10.4)[1] |

PPN: paternal pronucleus (pronuclei). No. of oocytes with PPN and monospermic fertilization were calculated from penetrated oocytes. The asterisk indicates significant difference at $P<0.05$. [1]Number/% of monospermic fertilization is lower with the supplement of the invention as a result of an increased fertilizing ability of sperm cells, resulting in higher penetration rate and higher polyspermic fertilization in the presence of compound of invention.

Different superscripts indicates significant difference at $P<0.05$ among experimental groups (in columns). Resveratrol, a polyphenol of red grapes with activities synergistic to the compound of invention was used for comparison, to show that the compound of the invention is even more efficient than naturally occurring polyphenols.

The invention includes culture media comprising N-benzyl-3,5-dicarbethoxy-4-phenyl-1,4-dihydropyridine. For example, a sterile culture media comprising a buffer solution (e.g. a basic salt solution), and/or one or more salts, and/or one or more amino acids, and N-benzyl-3,5-dicarbethoxy-4-phenyl-1,4-dihydropyridine.

The invention includes, without limitation, methods comprising surgically (or by necropsy) collecting unfertilized oocytes from a female subject (human or animal), which may optionally be stimulated to overproduce oocytes by known pharmaceutical and hormonal methods. The oocytes may optionally be frozen, stored, and then thawed when needed and before fertilization. Typically, oocytes are then fertilized in vitro. For example, the oocytes may be mixed and incubated with spermatozoa from a male subject in culture conditions, preferably washed and/or concentrated spermatozoa. Other fertilization approaches are also possible, such as intracytoplasmic sperm injection ("ICSI") where spermatozoa are selected and injected into oocytes using a needle.

After or during fertilization, oocytes (and potentially sperm) are transferred to an incubator and cultured in culture media where, ideally, fertilized oocytes develop into healthy embryos. Culture media including N-benzyl-3,5-dicarbethoxy-4-phenyl-1,4-dihydropyridine can be advantageously used for this incubation stage. The media may be refreshed during the incubation process.

Low oxygen IVF incubator conditions may be used, for example, 5% $CO_2$ and 5% $O_2$ atmosphere, 37 degrees Centigrade, and 100% relative humidity. Preferred incubation conditions may include some or all of the following:
  Reduced oxygen below natural atmospheric levels, less than 20% $O_2$, less than 10% $O_2$, 1%-20% $O_2$, or 1%-10% $O_2$.
  Elevated $CO_2$ above natural atmospheric levels, greater than 1% $CO_2$, greater than 3% $CO_2$, 1%-10% $CO_2$, or 3%-8% $CO_2$.
  Supplemented humidity above atmospheric levels, at least 80% relative humidity, at least 90% relative humidity, and 80%-100% relative humidity.
  Approximately body temperature (e.g. +/−1 degree C. or +/−3 degrees C. compared to body temperature or uterine temperature) for the mammalian animal species

TABLE 3

Embryonic development and blastocyst formation after 144 hr IVC in the presence of the compounds listed in the table

|  |  | No. of fertilized oocytes | No. of cleaved oocytes (mean % ± SEM) | No. of blastocysts (mean % ± SEM) | Mean cell No. per blastocyst (mean ± SEM) |
|---|---|---|---|---|---|
| DMSO (%, [v/v]) | 0.5 | 38 | 28 (65.9 ± 8.3)[a] | 2 (5.2 ± 2.9)[bc] | 36.0 ± 5.0[a] |
| Resveratrol ($\mu$M) | 3 | 67 | 47 (67.7 ± 10.6)[a] | 4 (6.2 ± 2.8)[bc] | 39.3 ± 11.3[a] |
| N-benzyl-3,5-dicarbethoxy-4-phenyl-1,4-dihydropyridine ($\mu$M) | 1.5 | 67 | 47 (70.2 ± 7.3)[a] | 10 (14.5 ± 7.2)[bc] | 32.7 ± 2.5[a] |
|  | 3 | 68 | 44 (62.7 ± 7.1)[a] | 18 (32.9 ± 8.1)a | 38.4 ± 4.2[a] | being cultured. For example, with human embryos, 36-38 degrees C., or 35-40 degrees C.

The fertilized oocytes are preferably incubated media including N-benzyl-3,5-dicarbethoxy-4-phenyl-1,4-dihydropyridine until a desired stage, with healthy living embryos or blastocysts identified and saved while any dead, unfertilized, or stalled oocytes/embryos are discarded. For example, the embryos may be cultured until 4-16 cell stages, 4-32 cell stages, 8-32 cell stages, at least 4 cell stage, at least 8 cell stage, or until blastocyst stage. Living embryos may then be transferred into the uterus of an adult female subject for implantation and gestation, preserved by freezing, or used for another purpose such as research.

The invention includes a preferred process A for in vitro cultivation of mammalian embryos, comprising the step of cultivating mammalian embryos from fertilized oocyte stage to blastocyst stage in the presence of N-benzyl-3,5-dicarbethoxy-4-phenyl-1,4-dihydropyridine. Preferred embodiments include the process of process A, wherein N-benzyl-3,5-dicarbethoxy-4-phenyl-1,4-dihydropyridine is used in the concentration of 0.3 to 30 µM.

Preferred embodiments include the process of process A, wherein N-benzyl-3,5-dicarbethoxy-4-phenyl-1,4-dihydropyridine is used in the concentration of 0.3 to 3 µM.

Preferred embodiments include the process of process A, wherein the mammalian embryos are selected from the group consisting of porcine embryos, murine embryos, rat embryos, equine embryos, canine embryos, cat embryos, goat embryos, sheep embryos, cattle embryos, human embryos.

The invention includes use of N-benzyl-3,5-dicarbethoxy-4-phenyl-1,4-dihydropyridine for cultivation of mammalian embryos from fertilized oocyte stage to blastocyst stage.

The invention includes use of N-benzyl-3,5-dicarbethoxy-4-phenyl-1,4-dihydropyridine for cultivation of mammalian embryos from fertilized oocyte stage to blastocyst stage, wherein N-benzyl-3,5-dicarbethoxy-4-phenyl-1,4-dihydropyridine is used in the concentration of 0.3 to 30 µM.

The invention includes use of N-benzyl-3,5-dicarbethoxy-4-phenyl-1,4-dihydropyridine for cultivation of mammalian embryos from fertilized oocyte stage to blastocyst stage, wherein N-benzyl-3,5-dicarbethoxy-4-phenyl-1,4-dihydropyridine is used in the concentration of 0.3 to 3 µM. In further preferred methods N-benzyl-3,5-dicarbethoxy-4-phenyl-1,4-dihydropyridine is used in a concentration of 0.3 to 30 µM, 0.3 to 10 µM, or 0.3 to 5 µM.

The invention includes use of N-benzyl-3,5-dicarbethoxy-4-phenyl-1,4-dihydropyridine for cultivation of mammalian embryos from fertilized oocyte stage to blastocyst stage, wherein the mammalian embryos are selected from the group consisting of porcine embryos, mammalian embryos, murine embryos, rat embryos, equine embryos, canine embryos, cat embryos, goat embryos, sheep embryos, cattle embryos or human embryos.

The invention includes culture medium for cultivating mammalian embryos from fertilized oocyte stage to blastocyst stage, which comprises N-benzyl-3,5-dicarbethoxy-4-phenyl-1,4-dihydropyridine as a supplement.

The invention includes culture medium for cultivating mammalian embryos from fertilized oocyte stage to blastocyst stage, wherein N-benzyl-3,5-dicarbethoxy-4-phenyl-1,4-dihydropyridine is present in the concentration of 0.3 to 30 µM.

The invention includes culture medium for cultivating mammalian embryos from fertilized oocyte stage to blastocyst stage, wherein N-benzyl-3,5-dicarbethoxy-4-phenyl-1,4-dihydropyridine is present in the concentration of 0.3 to 3 µM, or 0.3 to 5 µM, or 0.3 to 10 µM, or 0.3 to 30 µM, and methods and kits using such media.

The invention includes culture medium for cultivating mammalian embryos from fertilized oocyte stage to blastocyst stage, which is Porcine zygote medium 3 (PZM3) medium supplemented with N-benzyl-3,5-dicarbethoxy-4-phenyl-1,4-dihydropyridine.

The invention includes culture medium for cultivating mammalian embryos from fertilized oocyte stage to blastocyst stage, wherein the mammalian embryos are selected from the group consisting of porcine embryos, mammalian embryos, murine embryos, rat embryos, equine embryos, canine embryos, cat embryos, goat embryos, sheep embryos, cattle embryos, human embryos.

The invention also includes a kit comprising a culture medium for in vitro cultivating mammalian embryos from the zygote stage to the blastocyst stage, and at least N-benzyl-3,5-dicarbethoxy-4-phenyl-1,4-dihydropyridine as a supplement.

REFERENCES

Gardner D K & Lane M (2007) Embryo Culture Systems. In: GARDNER D. K. 2007: In vitro fertilization: a practical approach, 1st edition. New York: Informa Healthcare USA, Inc. 529 pp. ISBN:978-0-8493-3335-4. p. 221-282.

Chatot C L, Ziomek C A, Bavister B D, Lewis J L, Torres I (1989) An improved culture medium supports development of random-bred 1-cell mouse embryos in vitro. J Reprod Fertil. 2:679-88.

Kwon W S, Park Y J, Kim Y H, You Y A, Kim I C, Pang M G (2013) Vasopressin effectively suppresses male fertility. PLoS One: e54192.

Petters R M, Wells K D (1993) Culture of pig embryos. J Reprod Fertil Suppl. 48:61-73.

Shemesh M, Milaguir F, Ayalon N, Hansel W (1979) Steroidogenesis and prostaglandin synthesis by cultured bovine blastocysts. J Reprod Fertil. 56:181-5.

Summers M C (2013) A brief history of the development of the KSOM family of media. J Assist Reprod Genet. 8:995-9.

Yoshioka K, Suzuki C, Tanaka A, Anas I M, Iwamura S (2002) Birth of piglets derived from porcine zygotes cultured in a chemically defined medium. Biol Reprod 66:112-119.

The invention claimed is:

1. A method for in vitro cultivation of a mammalian embryo, comprising the step of incubating a fertilized oocyte in a culture medium containing N-benzyl-3,5-dicarbethoxy-4-phenyl-1,4-dihydropyridine at least up to blastocyst stage.

2. The method of claim 1, wherein the N-benzyl-3,5-dicarbethoxy-4-phenyl-1,4-dihydropyridine is used in a concentration of 0.3 to 30 µM.

3. The method of claim 1, wherein the N-benzyl-3,5-dicarbethoxy-4-phenyl-1,4-dihydropyridine is used in a concentration of 0.3 to 5 µM.

4. The method of claim 1, wherein the mammalian embryo is selected from the group consisting of porcine embryos, murine embryos, rat embryos, equine embryos, canine embryos, cat embryos, goat embryos, sheep embryos, cattle embryos, and human embryos.

5. A culture medium for cultivating mammalian embryos, comprising a culture medium and N-benzyl-3,5-dicarbethoxy-4-phenyl-1,4-dihydropyridine as a supplement, wherein N-benzyl-3,5-dicarbethoxy-4-phenyl-1,4-dihydropyridine is present in a concentration of 0.3 to 30 μM.

6. The culture medium of claim 5, wherein the N-benzyl-3,5-dicarbethoxy-4-phenyl-1,4-dihydropyridine is present in a concentration of 0.3 to 5 μM.

7. The culture medium of claim 5, wherein the culture medium is Porcine zygote medium 3 supplemented with the N-benzyl-3,5-dicarbethoxy-4-phenyl-1,4-dihydropyridine.

8. The culture medium of claim 5, the culture medium comprising water, one or more salts, one or more amino acids, and 0.3 to 10 μM of the N-benzyl-3,5-dicarbethoxy-4-phenyl-1,4-dihydropyridine.

9. The culture medium of claim 5, the culture medium comprising a basic salt solution as a buffer, one or more amino acids, and 0.3 to 30 μM of the N-benzyl-3,5-dicarbethoxy-4-phenyl-1,4-dihydropyridine.

10. A kit for in vitro cultivation of mammalian embryos, the kit comprising the culture medium according to claim 5.

11. A method for in vitro cultivation of a mammalian embryo, the method comprising:
retrieving an oocyte from a mammalian female;
fertilizing the oocyte to provide a fertilized oocyte, the fertilization comprising one of incubating the oocyte with mammalian sperm and injecting a mammalian sperm into the oocyte;
after said fertilization, culturing the fertilized oocyte in culture media comprising N-benzyl-3,5-dicarbethoxy-4-phenyl-1,4-dihydropyridine, wherein the culturing step continues for more than three days, and the fertilized oocyte matures into a blastocyst during the culturing step.

12. The method of claim 11, wherein the oocyte is a human oocyte; and wherein the culturing step takes place in an incubator, and wherein the incubator maintains a temperature in the range of 35-40 degrees Celsius.

13. The method of claim 11, further comprising:
after said fertilization step, transferring the mammalian embryo into a mammalian uterus.

14. The method of claim 11, wherein the culturing step takes place in an incubator and continues for at least three days.

15. The method of claim 11, wherein the culture media comprises the N-benzyl-3,5-dicarbethoxy-4-phenyl-1,4-dihydropyridine in a concentration of 0.3 to 30 μM.

16. The method of claim 11, wherein the culture media comprises the N-benzyl-3,5-dicarbethoxy-4-phenyl-1,4-dihydropyridine in a concentration of 0.3 to 10 μM.

17. The method of claim 11, wherein the culture media comprises a buffer, one or more amino acids, and the N-benzyl-3,5-dicarbethoxy-4-phenyl-1,4-dihydropyridine in a concentration of 0.3 to 30 μM.

18. The method of claim 11 wherein the mammalian embryo is selected from the group consisting of porcine embryos, murine embryos, rat embryos, equine embryos, canine embryos, cat embryos, goat embryos, sheep embryos, cattle embryos, and human embryos.

* * * * *